(12) United States Patent
Mundis, Jr. et al.

(10) Patent No.: US 11,246,629 B2
(45) Date of Patent: Feb. 15, 2022

(54) TRANSVERSE CONNECTOR

(71) Applicant: K2M, Inc., Leesburg, VA (US)

(72) Inventors: Gregory Mundis, Jr., San Diego, CA (US); Han Jo Kim, NY, NY (US); John Ferguson, Auckland (NZ); Laurel Blakemore, Williston, FL (US); Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 128 days.

(21) Appl. No.: 16/500,568

(22) PCT Filed: Apr. 9, 2018

(86) PCT No.: PCT/US2018/026673
§ 371 (c)(1),
(2) Date: Oct. 3, 2019

(87) PCT Pub. No.: WO2018/187797
PCT Pub. Date: Oct. 11, 2018

(65) Prior Publication Data
US 2020/0100816 A1 Apr. 2, 2020

Related U.S. Application Data

(60) Provisional application No. 62/482,977, filed on Apr. 7, 2017.

(51) Int. Cl.
*A61B 17/70* (2006.01)
*A61B 17/88* (2006.01)
(Continued)

(52) U.S. Cl.
CPC ...... *A61B 17/7052* (2013.01); *A61B 17/7091* (2013.01); *A61B 17/8869* (2013.01);
(Continued)

(58) Field of Classification Search
CPC ............ A61B 17/7049; A61B 17/7052; A61B 17/7053; A61B 17/7082; A61B 17/7091;
(Continued)

(56) References Cited

U.S. PATENT DOCUMENTS

| 5,667,506 A | 9/1997 | Sutterlin |
| 6,110,173 A * | 8/2000 | Thomas, Jr. ....... A61B 17/7052 606/252 |

(Continued)

OTHER PUBLICATIONS

Extended European Search Report for EP18780775.5 dated Dec. 21, 2020; 3 pages.
International Search Report for PCT/US2018/026673 dated Jul. 19, 2018.

*Primary Examiner* — Pedro Philogene
(74) *Attorney, Agent, or Firm* — Lerner, David, Littenberg, Krumholz & Mentlik, LLP

(57) ABSTRACT

A transverse connector includes a cross member connecting assembly, and first and second spinal rod connection members rotatably coupled to opposing end portions of the cross member connecting assembly. The cross member connecting assembly includes a first band slot defined therethrough and a threaded opening extending through an upper surface of the cross member connecting assembly and into the first band slot. The cross member connecting assembly includes a band set screw threadingly engaged with the threaded opening and movable relative to the first band slot.

18 Claims, 15 Drawing Sheets

(51) Int. Cl.
*A61B 17/00* (2006.01)
*A61B 17/56* (2006.01)

(52) U.S. Cl.
CPC . *A61B 17/7082* (2013.01); *A61B 2017/00862* (2013.01); *A61B 2017/564* (2013.01)

(58) Field of Classification Search
CPC ............ A61B 17/7004; A61B 17/7019; A61B 17/7023; A61B 17/7032; A61B 17/7041; A61B 17/705; A61B 17/7055; A61B 17/8869; A61B 2017/00862; A61B 2017/564
See application file for complete search history.

(56) References Cited

U.S. PATENT DOCUMENTS

| | | | |
|---|---|---|---|
| 8,617,213 B2* | 12/2013 | Moore | A61B 17/7052 606/253 |
| 2004/0267259 A1 | 12/2004 | Mazda et al. | |
| 2007/0049932 A1 | 3/2007 | Richelsoph et al. | |
| 2007/0270803 A1* | 11/2007 | Giger | A61B 17/8076 606/60 |
| 2008/0306538 A1 | 12/2008 | Moore et al. | |
| 2011/0137345 A1* | 6/2011 | Stoll | A61B 17/7083 606/251 |
| 2012/0226316 A1 | 9/2012 | Dant et al. | |
| 2013/0072983 A1 | 3/2013 | Lindquist et al. | |
| 2015/0196328 A1 | 7/2015 | Hirschl et al. | |

* cited by examiner

TRANSVERSE CONNECTOR

CROSS-REFERENCE TO RELATED APPLICATION

This application is a national phase entry under 35 U.S.C. § 371 of International Application No. PCT/US2018/026673, filed Apr. 9, 2018, which claims the benefit of the filing date of U.S. Provisional Patent Application No 62/482,977, filed Apr. 7, 2017, the disclosures of which are hereby incorporated herein by reference.

TECHNICAL FIELD

The present disclosure relates generally to spinal fixation devices. More particularly, the present disclosure relates to transverse connectors that are adjustable and securable to spinal rods and bands, and systems and methods of using the same for spinal stabilization and support.

BACKGROUND

Disease, the effects of aging, or physical trauma resulting in damage to the spine has been treated in many instances by fixation or stabilization of the effected vertebra(e). A wide variety of spinal fixation apparatuses have been employed in surgical procedures for correcting spinal injuries and the effects of spinal diseases. Many of these apparatuses commonly use a pair of longitudinal link rods running in a relative parallel relationship to each other and the spinal column. These rods are connected to coupling elements, which in turn are secured to the underlying vertebral bone by spinal bone fixation fasteners such as pedicle screws, hooks, and the like. The pair of longitudinal link rods can be held in position relative to one another by transverse connectors, also known as transverse bridge elements or cross-connectors.

The natural anatomical variations in the spinal column of a subject are such that implanted spinal rods, while approximating a parallel relationship one to the other, can vary from that parallel relationship considerably and in multiple planes. For this reason, any transverse connector used to attach the two rods to each other should not be of a rigid design without the ability to be re-configured as needed during the process of implanting and attaching to the two opposing rods.

A multidirectional articulating transverse connector that can adapt to a wide variance in the contours of the spinal column is desirable. Further, a transverse connector that also has a low profile and a smooth contoured surface, thereby reducing the potentially negative impact of the implanted appliance on the overlying and surrounding soft tissue of the subject into which the appliance has been surgically implanted is also desirable. Further still, a transverse connector that is capable of being easily adjusted to increase or decrease the length between the two opposing bone connection points to accommodate natural anatomical variances and once selected, to lock or unlock the device in the selected configuration is also desirable.

Thus, a transverse connector that provides ease of operation by a surgeon to simultaneously adjust in multiple dimensions one spinal rod connecting end of the transverse connector in relation to the other spinal rod connecting end of the transverse connector and to provide a device having a low profile and smooth contours for surfaces in contact with adjacent soft tissue is desirable.

SUMMARY

In accordance with an aspect of the present disclosure, a transverse connector includes a cross member connecting assembly, and first and second spinal rod connection members rotatably coupled to opposing end portions of the cross member connecting assembly. The cross member connecting assembly includes a first band slot defined therethrough and a threaded opening extending through an upper surface of the cross member connecting assembly and into the first band slot. The cross member connecting assembly includes a band set screw threadingly engaged with the threaded opening and movable relative to the first band slot.

A band anvil may be non-rotatably coupled to the band set screw. The band anvil may include a plate disposed within the first band slot such that rotation of the band set screw results in the plate varying spacing within the first band slot. The band set screw may include a channel defined therein having an annular rim, and the band anvil may include a stem extending from the plate and having an annular flange. The stem may be positioned within the channel with the annular flange engaged with the annular rim.

The cross member connecting assembly may have a fixed length.

The cross member connecting assembly may include a second band slot defined therethrough and a second threaded opening extending through an upper surface of the cross member connecting assembly and into the second band slot. The cross member connecting assembly may include a second band set screw threadingly engaged with the second threaded opening and movable relative to the second band slot.

The cross member connecting assembly may include a first cross member and a second cross member slidably engaged with each other, and the first band slot may be defined in the first cross member. The second cross member may include a second band slot defined therethrough and a second threaded opening extending through an upper surface of the cross member connecting assembly and into the second band slot. The cross member connecting assembly may include a second band set screw threadingly engaged with the second threaded opening and movable relative to the second band slot.

The first cross member may include an elongated receiving arm and the second cross member may include an elongated insertion arm slidably disposed within a receiving passage of the elongated receiving arm. The elongated receiving arm may include a pin hole defined therethrough and the elongated insertion arm may include a pin slot defined therethrough, and a pin may be positioned through the pin hole and the pin slot such that the pin slidably translates longitudinally in the pin slot in response to sliding movement between the first and second cross members. The elongated insertion arm may include a threaded set screw receptacle defined therein, and a cross connector set screw may be rotatably coupled with the threaded set screw receptacle.

The opposing end portions of the cross member connecting assembly may include first and second articulating balls, respectively. The first articulating ball may be disposed within a first ball joint receptacle of the first spinal rod connection member and the second articulating ball may be disposed within a second ball joint receptacle of the second spinal rod connection member.

In accordance with another aspect of the present disclosure, a spinal fixation construct includes a plurality of bone screws, spinal rods, and a transverse connector. The transverse connector includes a cross member connecting assembly, and first and second spinal rod connection members rotatably coupled to opposing end portions of the cross member connecting assembly. The cross member connecting assembly includes a band slot defined therethrough and a threaded opening extending through an upper surface of the cross member connecting assembly and into the band slot. The cross member connecting assembly includes a band set screw threadingly engaged with the threaded opening and movable relative to the band slot. The first and second spinal rod connecting members include respective first and second spinal rod connection passages defined therethrough for selectively and releasably securing the spinal rods thereto.

The spinal fixation construct may include a band. The band may be positionable through the band slot of the cross member connecting assembly and securable therein by the band set screw. The spinal fixation construct may include a bone anchor. The band may include a central portion positionable around an eyelet of the bone anchor and end portions positionable through the band slot of the cross member connecting assembly.

In accordance with yet another aspect of the present disclosure, a method for spinal stabilization includes attaching a first spinal rod connection member of a transverse connector to a first spinal rod, attaching a second spinal rod connection member of the transverse connector to a second spinal rod, the first and second spinal rods disposed on opposed sides of a spinous process of a spine such that a cross member connecting assembly of the transverse connector extends between the first and second spinal rods, and adjusting a length of the cross member connecting assembly by sliding a first cross member relative to a second cross member of the cross member connecting assembly.

The method may include tightening spinal rod locking screws into respective first and second spinal rod locking screw receptacles of the first and second spinal rod connection members after attaching the first and second spinal rod connection members to the first and second spinal rods. The may including tightening a cross connector set screw into a threaded set screw receptacle of an elongated insertion arm of the second cross member that is disposed within a receiving passage of an elongated receiving arm of the first cross member after adjusting the length of the cross member connecting assembly.

The method may include looping a band around a lamina of the spine, and passing end portions of the band through a band slot defined through the cross member connecting assembly. The method may include tensioning the band, and tightening a band set screw into a threaded opening of the cross member connecting assembly. The threaded opening may extend into the band slot such that the band set screw is movable into the band slot to secure the end portions of the band within the band slot.

The method may further include placing bone anchors into a bony element of the spine, and passing a band through each of the bone anchors such that a central portion of each of the bands is looped around and eyelet of the respective bone anchor and end portions of the band are passed through band slots defined through the cross member connecting assembly.

In accordance with an aspect of the present disclosure, a kit includes a first transverse connector. The first transverse connector includes a cross member connecting assembly, and first and second spinal rod connection members rotatably coupled to opposing end portions of the cross member connecting assembly. The cross member connecting assembly includes a first band slot defined therethrough and a threaded opening extending through an upper surface of the cross member connecting assembly and into the first band slot. The cross member connecting assembly includes a band set screw threadingly engaged with the threaded opening and movable relative to the first band slot.

The kit may include a second transverse connector. The second transverse connector may include a cross member connecting assembly, and first and second spinal rod connection members rotatably coupled to opposing end portions of the cross member connecting assembly. The cross member connecting assembly may include a first band slot defined therethrough and a threaded opening extending through an upper surface of the cross member connecting assembly and into the first band slot. The cross member connecting assembly may include a band set screw threadingly engaged with the threaded opening and movable relative to the first band slot.

The first and second transverse connectors may have different lengths. The cross member connecting assembly of the first transverse connector may have a fixed length and the cross member connecting assembly of the second transverse connector may have a variable length.

The kit may include a plurality of bone screws, a plurality of spinal rods, and at least one band, and/or a driving instrument and a tensioning instrument.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Figure 1:
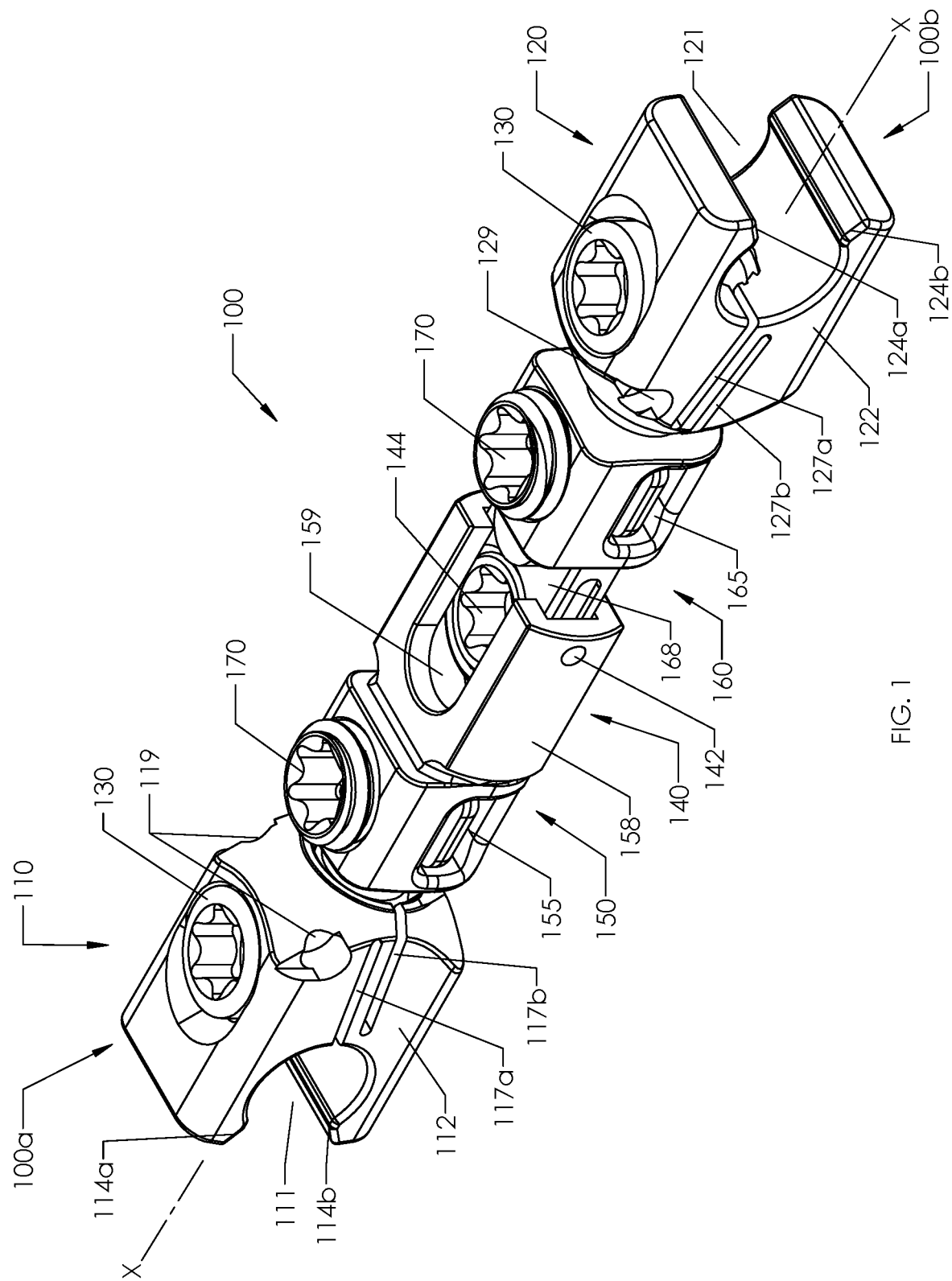
FIG. 1 is a perspective view of a transverse connector in accordance with an embodiment of the present disclosure.

Embodiments of the present disclosure are now described in detail with reference to the drawings in which like reference numerals designate identical or corresponding elements in each of the several views. Throughout this description, the term "proximal" refers to a portion of a system, a device, or a component thereof that is closer to a clinician, and the term "distal" refers to the portion of the system, device, or component thereof that is farther from the clinician. The term "clinician" refers to a doctor (e.g., a surgeon), a nurse, or any other care provider, and may include support personnel. Additionally, in the drawings and in the description that follows, terms such as "top," "bottom," "upper," and "lower," and similar directional terms are used simply for convenience of description and are not intended to limit the disclosure.

Exemplary embodiments of the present disclosure are discussed herein below in terms of transverse connectors for use with spinal rods, bands, and associated bone connection devices in a spinal fixation construct, and methods of using the same for stabilizing and/or fixing injured or diseased vertebrae.

Referring now to FIGS. 1-6, a transverse connector 100 in accordance with an embodiment of the present disclosure is shown. The transverse connector 100 includes first and second spinal rod connection members or polyaxial heads 110, 120 and a cross member connecting assembly or bridge assembly 140 connecting the first and second spinal rod connection members 110, 120.

The first and second spinal rod connection members 110, 120 (also referred to herein collectively as connection members) are disposed at opposing end portions 100a, 100b of the transverse connector 100. Each of the connection members 110, 120 includes a body 112, 122 having an outer or first portion 112a, 122a defining first and second spinal rod connection passages 111, 121, respectively, therethrough. The first and second spinal rod connection passages 111, 121 (also referred to herein collectively as connection passages) are each configured to be selectively and releasably secured to a spinal rod 4 (FIG. 7) which, in turn, can be secured to the underlying bone of a patient's or subject's spinal column.

The connection passages 111, 121 are open laterally toward the respective end portions 100a, 100b of the transverse connector 100, and include an upper retention lip 114a, 124a and a lower retention lip 114b, 124b which project towards one another about outer edges of the connection passages 111, 121. The upper retention lip 114a, 124a and the lower retention lip 114b, 124b narrow the respective connection passage 111, 121 and thus, facilitate and/or enhance the spinal rod retention capability of the connection passages 111, 121. It should be understood that the connection passages 111, 121 may include the upper retention lip 114a, 124a and/or the lower retention lip 114b, 124b in a variety of configurations to aid in the retention of a spinal rod therein.

Figure 2:
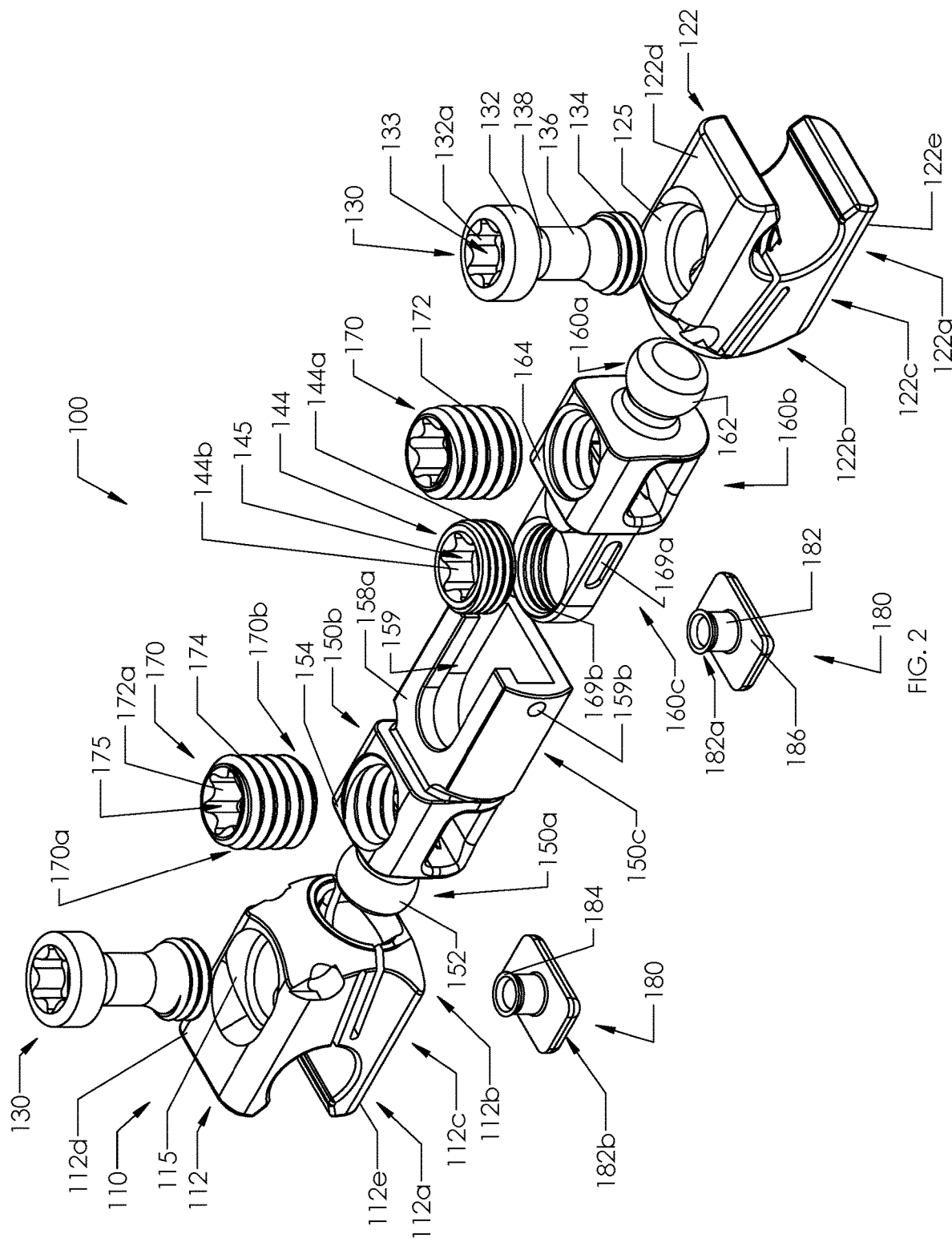
FIG. 2 is a perspective view, with parts separated, of the transverse connector of FIG. 1.
Figure 3:
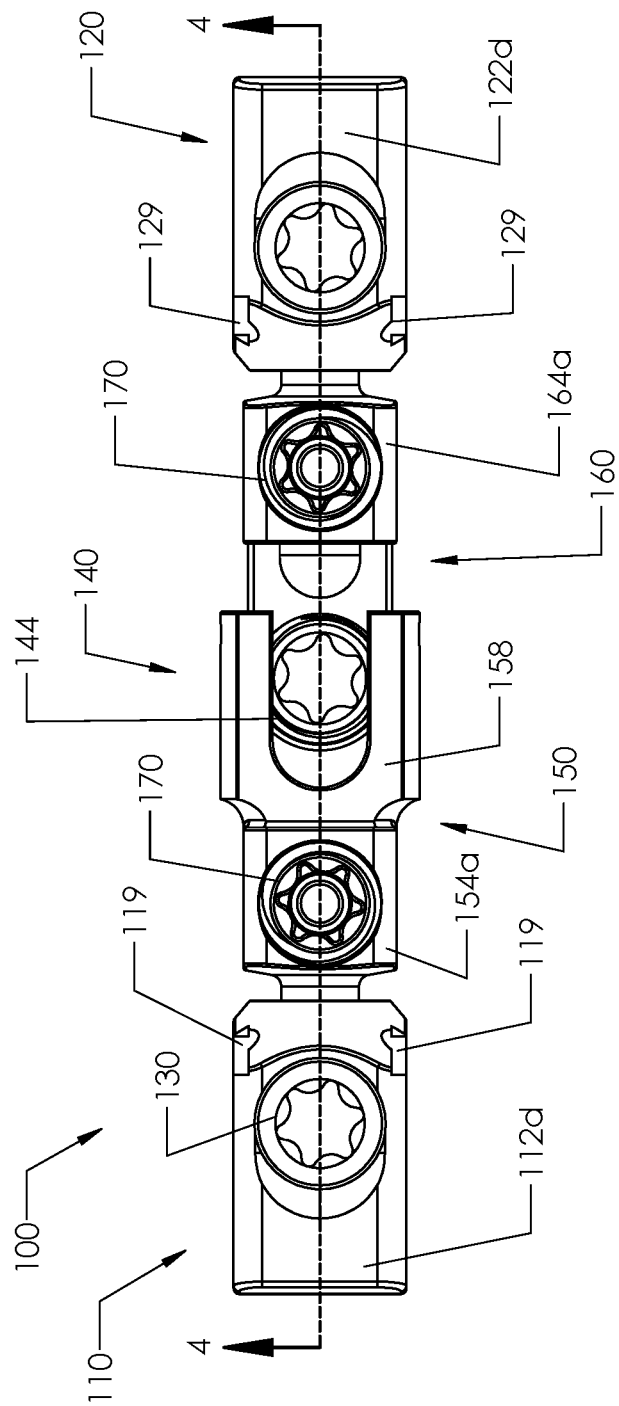
FIG. 3 is a top view of the transverse connector of FIG. 1.
Figure 4:
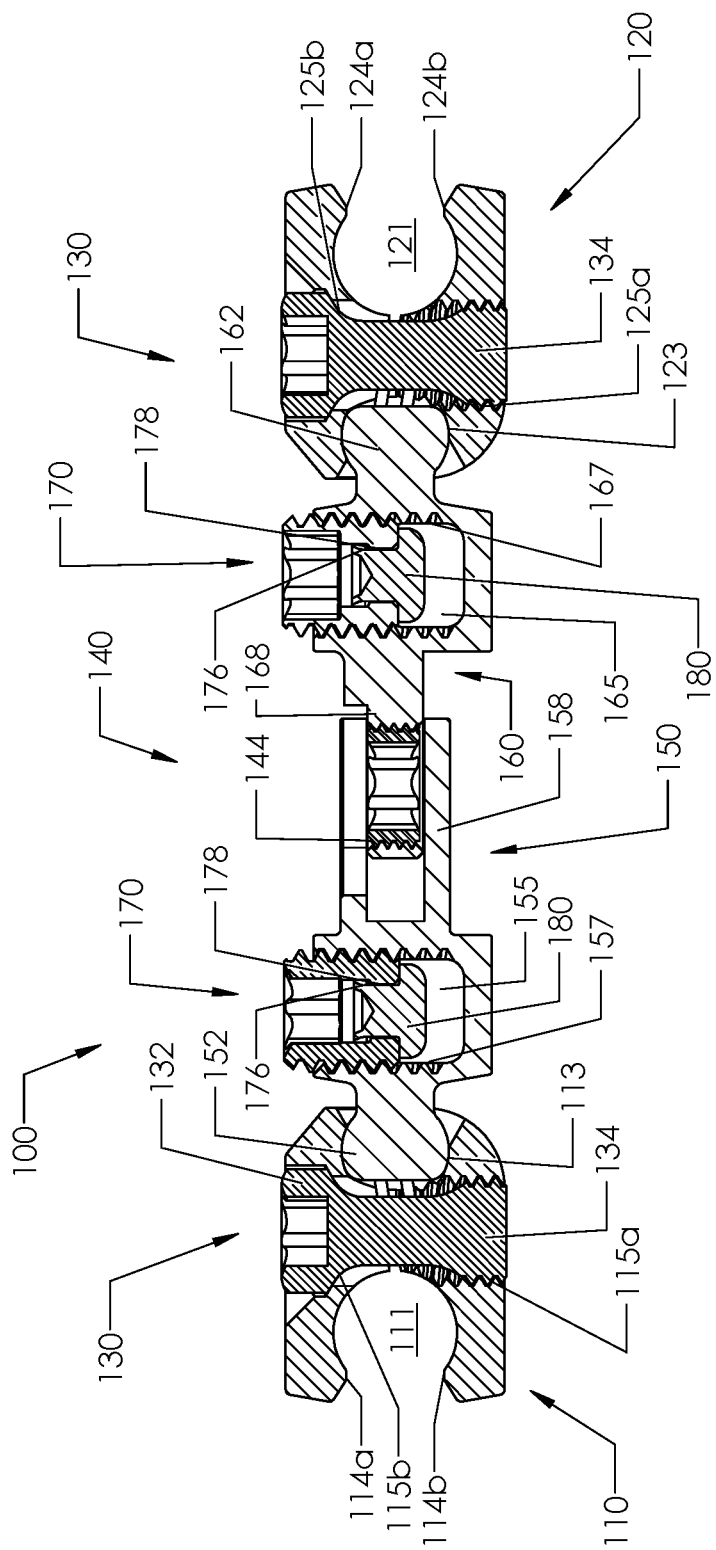
FIG. 4 is a cross-sectional view of the transverse connector of FIG. 1, taken along section line 4-4 of FIG. 3.
Figure 5:
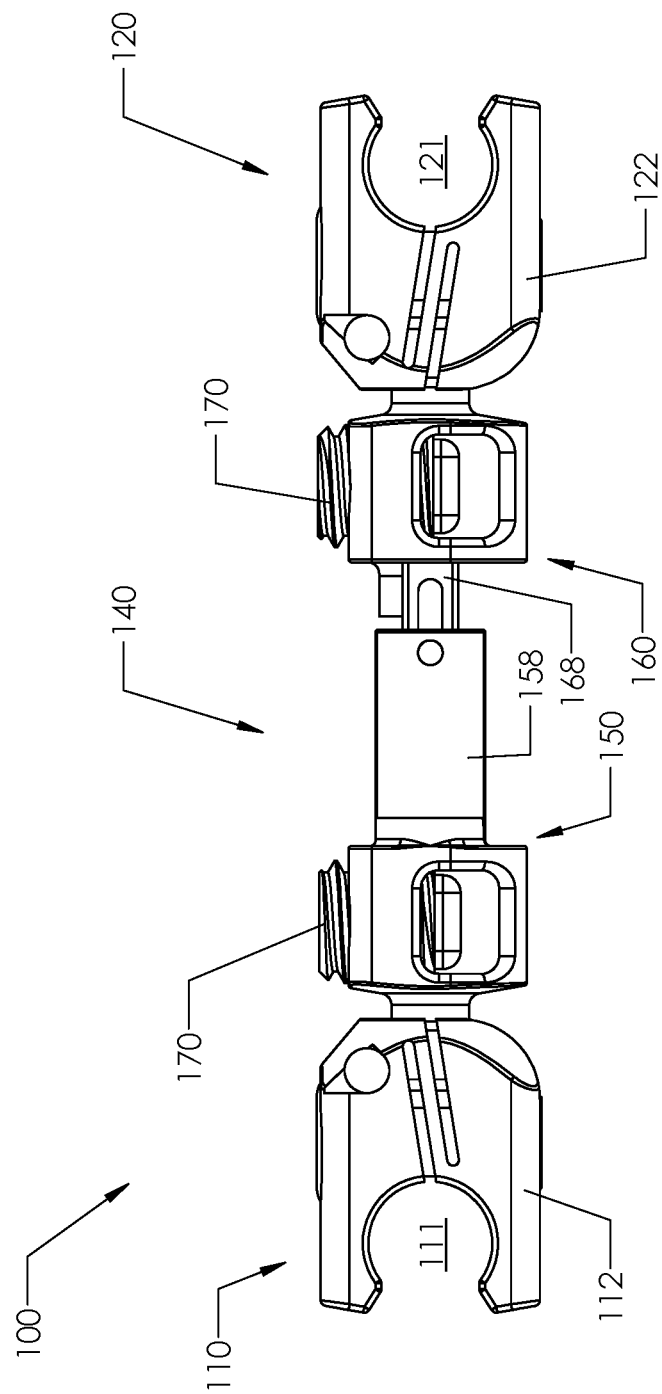
FIG. 5 is a side view of the transverse connector of FIG. 1.
Figure 6:
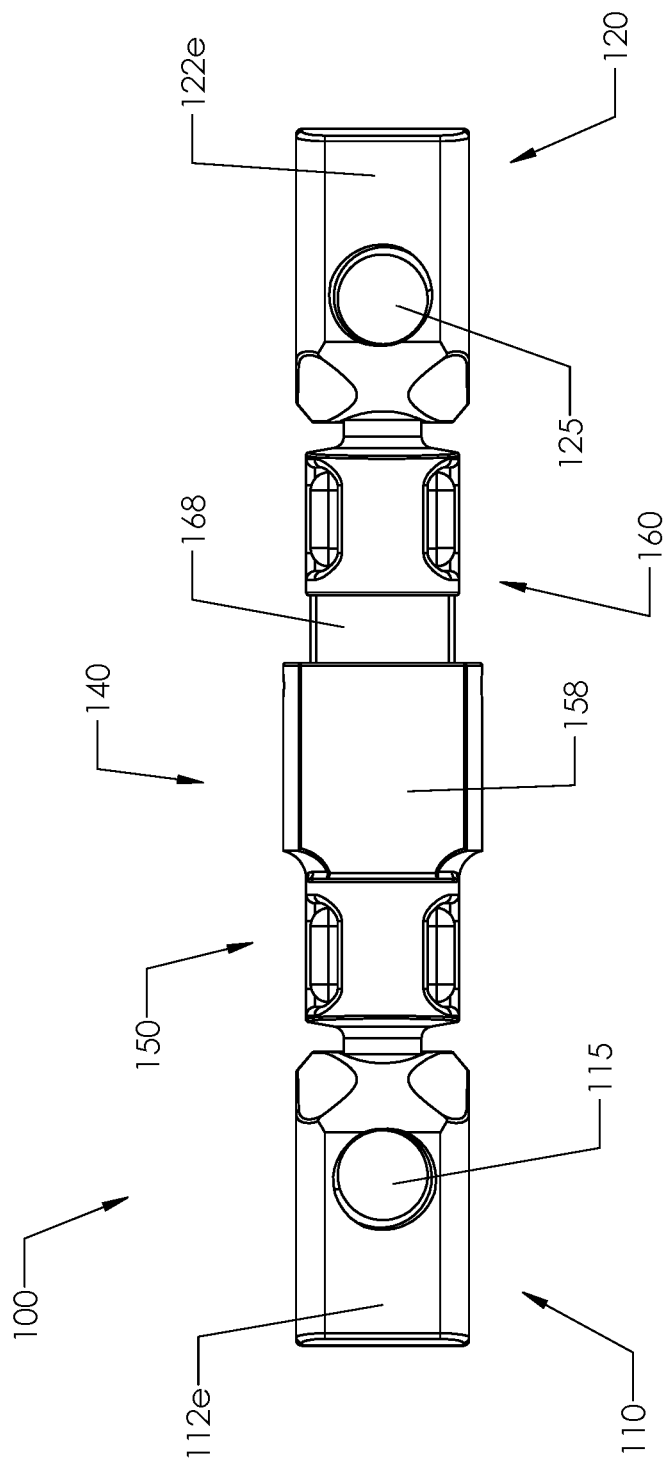
FIG. 6 is a bottom view of the transverse connector of FIG. 1.

As best seen in FIGS. 2 and 4, the body 112, 122 of the respective connection members 110, 120 has an inner or second portion 112b, 122b defining first and second ball joint receptacles 113, 123, respectively, therein. Each of the first and second ball joint receptacles 113, 123 (also referred to herein collectively as ball joint receptacles) is an opening configured and dimensioned to receive a correspondingly sized first or second articulating ball 152, 162 of the cross member connecting assembly 140 therein by, for example, a snap-fit connection.

The body 112, 122 of the respective connection members 110, 120 has a middle or third portion 112c, 122c defining first and second spinal rod locking screw receptacles 115, 125 therein. Each of the first and second spinal rod locking screw receptacles 115, 125 (also referred to herein collectively as locking screw receptacles) extends through an upper surface 112d, 122d and a lower surface 112e, 122e of the respective body 112, 122 of the connection members 110, 120, and is configured and dimensioned to receive a spinal rod locking screw 130 therein.

As best seen in FIG. 4, each of the locking screw receptacles 115, 125 is provided with a threaded portion 115a, 125a only in a lower portion of the respective locking screw receptacles 115, 125, that is, the portion of the locking screw receptacle 115, 125 that is below the elevation of the connection passages 111, 121. An upper portion of the locking screw receptacle 115, 125, located above the level of the connection passage 111, 121, is unthreaded but provided with an inwardly directed annular restricting ledge 115b, 125b that is sized and configured to permit free passage of the spinal rod locking screw 130 therethrough until a threaded tail portion 134 of the locking screw 130 engages the threaded portion 115a, 125a of the locking screw receptacle 115, 125.

Figure 14:
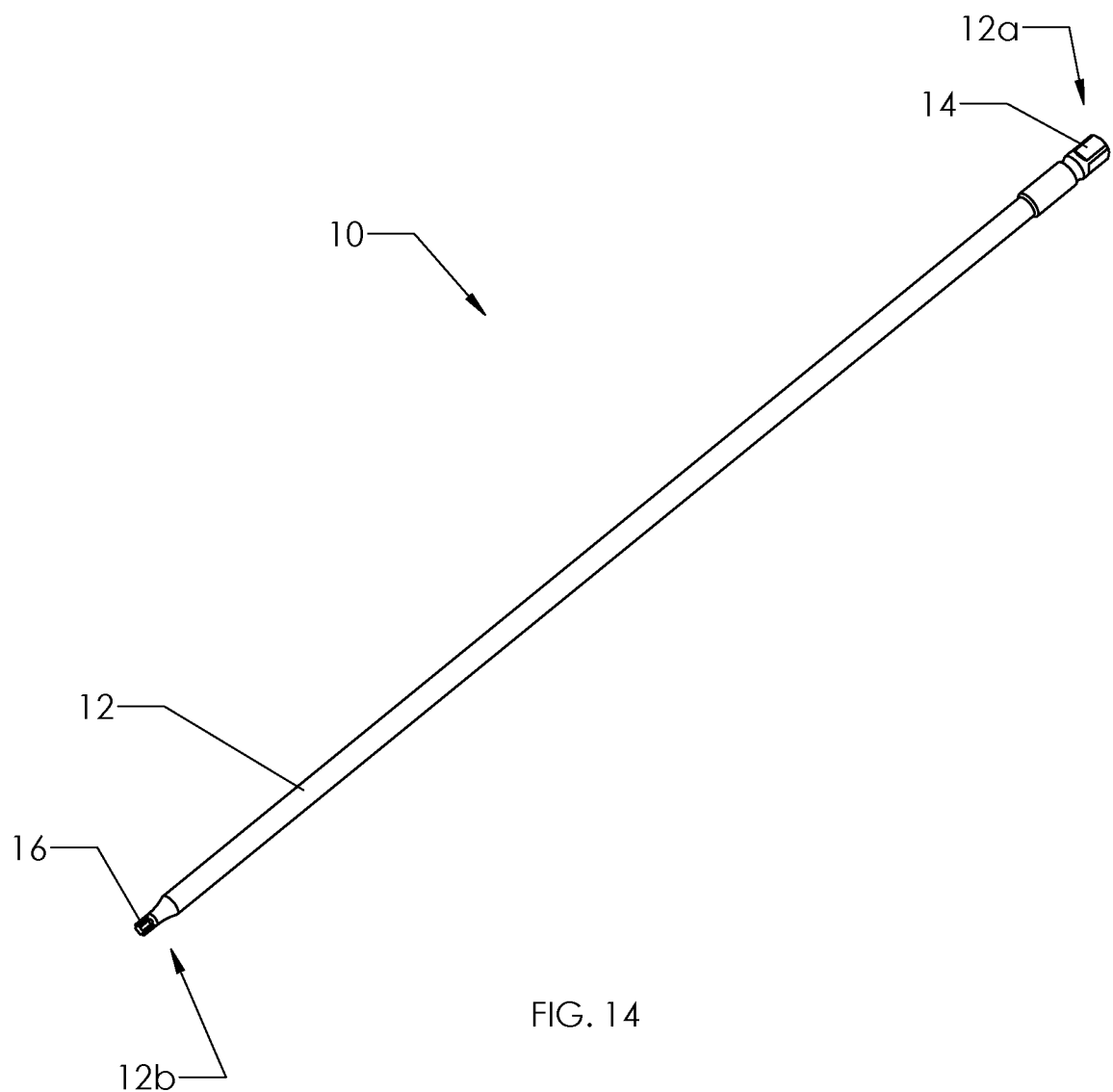
FIG. 14 is a perspective view of a driving instrument suitable for use with the transverse connectors of FIGS. 1 and 9 in accordance with an embodiment of the present disclosure.

As best seen in FIG. 2, each of the spinal rod locking screws 130 includes a head portion 132, a threaded tail portion 134, and a body portion 136 interconnecting the head portion 132 and the threaded tail portion 134. The head portion 132 includes a recess 133 defined therein that is configured to mate with a driving instrument 10 (FIG. 14). The head portion 132 includes gripping elements 132a located within the recess 133 that have a complementary configuration to the driving instrument 10 to control the insertion and/or advancement, as well as retraction and/or withdrawal, of the spinal rod locking screw 130 into the locking screw receptacle 115, 125 of the respective connection member 110, 120. The gripping elements 132a may be multi-faceted (e.g., hexagonal or hexolobular in shape), keyed, or any other suitable configuration that is engageable with a suitable driving instrument. The spinal rod locking screw 130 further includes an outwardly directed flange 138 on an underside of the head portion 132.

In operation, the threaded tail portion 134 of the spinal rod locking screw 130 is inserted through the upper surface 112d, 122d of the respective body 112, 122 and into the locking screw receptacle 115, 125. As the threaded tail portion 134 of the spinal rod locking screw 130 is threaded into the threaded portion 115a, 125a of the locking screw receptacle 115, 125, the outwardly directed flange 138 of the spinal rod locking screw 130 is brought into contact with the inwardly directed annular restricting ledge 115b, 125b of the spinal rod locking screw receptacle 115, 125 such that the outwardly directed flange 138 exerts compressive forces against the inwardly directed annular restricting ledge 115b, 125b. An upper extent of the spinal rod locking screw 130, when fully seated within the locking screw receptacle 115, 125, is approximately flush with or below the level of the upper surface 112e, 122e of the connection member 110, 120 so as to provide a low profile for the transverse connector 100 and thus, reduce contact and trauma that might be imposed on overlying soft tissue of a subject.

As shown in FIG. 1, the body 112, 122 of each of the connection members 110, 120 includes a first compression slot 117a, 127a and a second compression slot 117b, 127b defined therein. The first compression slot 117a, 127a and the second compression slot 117b, 127b pass over each other through only a limited portion of the body 112, 122 in opposing directions. By configuring the first compression slot 117a, 127a and the second compression slot 117b, 127b in paired overlying relation having opposing sides of origin and thus, opposing directions of penetration into the body 112, 122, the connection members 110, 120 can react to the above described compressive forces of the spinal rod locking screw 130 so as to bring those compressive forces to bear on both the connection passages 111, 121 and the ball joint receptacles 113, 123.

Figure 7:
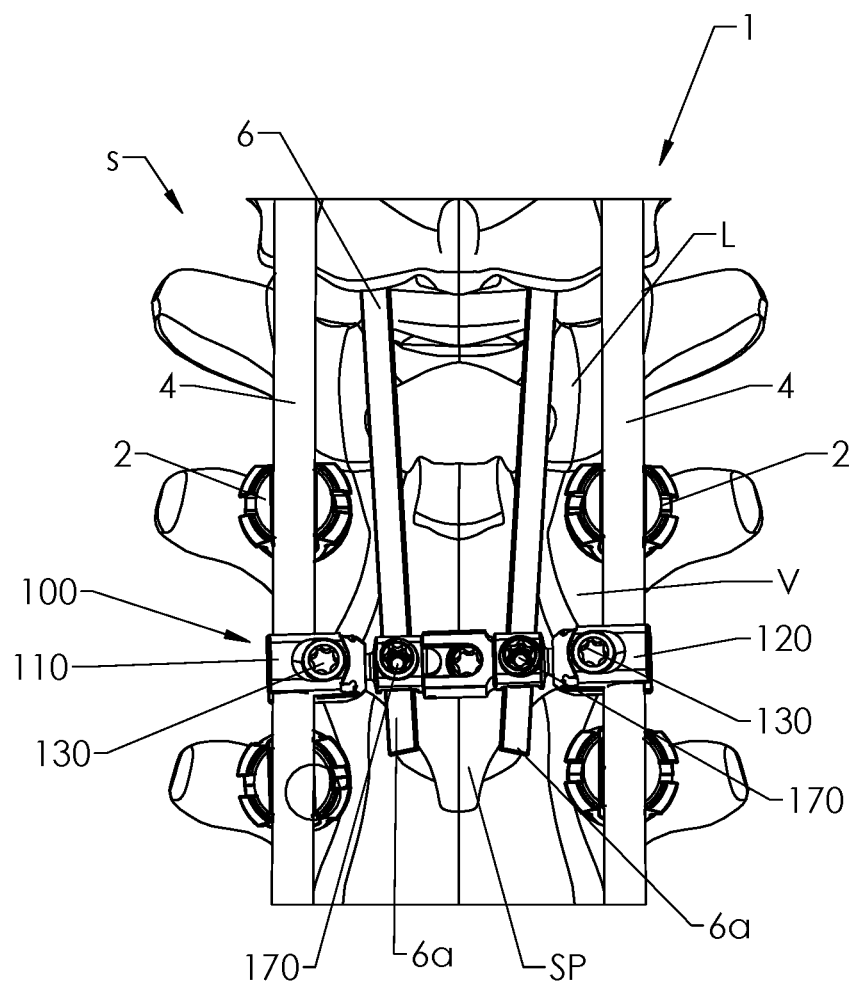
FIG. 7 is a perspective view of a spinal fixation system attached to a spine in accordance with an embodiment of the present disclosure.

Each of the connection members 110, 120 is provided with at least one and, as shown in the illustrated embodiment, two opposing grasping recesses 119, 129 which are sized and configured to receive a grasping instrument (not shown) used by a clinician to securely and releasably grasp each of the connection members 110, 120 for purposes of manipulating the connection members 110, 120 into a proper engaging relationship with a respective spinal rod 4 (FIG. 7). The grasping recesses 119, 129 can be of any configuration suitable for receiving the grasping instrument. The grasping recesses 119, 129 can alternatively be configured as protrusions or any other desired configuration so long as they facilitate the grasping and manipulation of the connection members 110, 120 by a clinician during the implantation of the transverse connector 100.

The connection members 110, 120 are connected to one another by the cross member connecting assembly 140. The cross member connecting assembly 140 includes a first cross member 150 and a second cross member 160. Each of the first and second cross members 150, 160 (also referred to herein collectively as cross members) includes an outer or first portion 150a, 160a including first and second articulating balls 152, 162. The first and second articulating balls 152, 162 are sized and configured to fit into and articulate within the respective ball joint receptacle 113, 123 of the connection members 110, 120 as shown in FIG. 4.

Each of the cross members 150, 160 includes a second or middle portion 150b, 160b including a body 154, 164 defining a band slot 155, 165 therethrough. The band slots 155, 165 are configured to be selectively and releasably secured to a band 6 (FIG. 7) which, in turn, can be secured to the underlying bone of a subject's spinal column. The band slots 155, 165 extend laterally through the respective body 154, 164 of the cross members 150, 160 (e.g., through side surfaces thereof) along an axis that is substantially orthogonal to the longitudinal axis "X" defined through the transverse connector 100 such that bands 6 (FIG. 7) are positionable laterally therethrough.

The body 154, 164 of each of the cross members 150, 160 also includes a threaded opening 157, 167 extending through an upper surface 154a, 164a of the respective body 154, 164 of the cross members 150, 160 into the band slots 155, 165. The threaded opening 157, 167 is configured to threadingly engage a band set screw 170 therein to secure a band in the band slot 155, 165 via engagement with a band anvil 180.

As best seen in FIG. 2, each of the band set screws 170 includes a body 172 having a cylindrical shape and including threads 174 disposed on an external surface thereof. A recess 175 is defined in a first end 170a of the band set screw 170 and is configured to mate with a driving instrument 10 (FIG. 14). Gripping elements 172a are located within the recess 175 that have a complementary configuration to the driving instrument (not shown) to control the insertion and/or advancement, as well as retraction and/or withdrawal, of the band set screw 170 into the respective cross member 150, 160. The gripping elements 172a may be multi-faceted (e.g., hexagonal or hexolobular in shape), keyed, or any other suitable configuration that is engageable with a suitable driving instrument. As best seen in FIG. 4, the band set screw 170 also includes a channel 176 defined in a second end 170b of the body 172. The channel 176 includes an annular rim 178 extending there within.

A band anvil 180 is coupled to the band set screw 170. The band anvil 180 includes a stem 182 having a cylindrical shape and including an annular flange 184 disposed at a first end 182a of the stem 182 and a plate 186 disposed at a second end 182b of the stem 182. The band anvil 180 is coupled to the respective band set screw 170 by positioning the band anvil 180 within the band slot 155, 165 and passing the band set screw 170 through the upper surface 154a, 164a of the respective body 154, 164 and into the threaded opening 157, 167 of the body 154, 164. As the body 172 of the band set screw 170 is threaded into the threaded opening 157, 167 of the cross member 150, 160, the stem 182 of the band anvil 180 passes into the channel 176 of the band set screw 170 until the flange 184 of the band anvil 180 engages the annular rim 178 of the band set screw 170.

In operation, as the band set screw 170 is rotated within the threaded opening 157, 167 of the cross member 140, 150, the band anvil 180, which is non-rotatably coupled thereto, moves within the band slot 155, 165 to vary the spacing defined therein and to exert a compressive force against the band 6 positioned therethrough (FIG. 7). An upper extent of the band set screw 170, when fully seated within the threaded opening 157, 167, is approximately flush with or below the level of the upper surface 154a, 164a of the respective cross member 150, 160 so as to provide a low profile for the transverse connector 100 and thus, reduce contact and trauma that might be imposed on overlying soft tissue of a subject.

The first cross member 150 includes a third or inner portion 150c including an elongated receiving arm 158 configured as an external sleeve having an internally defined receiving passage 159 having a partially open top surface 158a. The elongated receiving arm 158 and the receiving passage 159 each have a generally flattened shape which serve to promote a lower profile for the transverse connector 100. Other configurations, however, are envisioned, such as a rounded, ovoid, square, or other shape.

The second cross member 160 includes a third or inner portion 160c including an elongated insertion arm 168 configured to correspond to the shape of the receiving passage 159 of the elongated receiving arm 158 of the first cross member 150. The elongated insertion arm 168 has a generally flattened shape, however, the elongated insertion arm 168 may have any shape complementary to the receiving passage 159 of the elongated receiving arm 158 of the first cross member 150. The elongated insertion arm 168 of the second cross member 160 thus slidably passes into the complimentary shaped receiving passage 159 of the first cross member 150. By this sliding operation of the elongated insertion arm 168 inward or outward within the elongated receiving arm 158, the length of the cross member connecting assembly 140 and therefore the length of the transverse connector 100 can be selectively lengthened or shortened. Additionally, the complementary configuration between the elongated insertion arm 168 and the receiving passage 159 of the elongated receiving arm 158 inhibits relative rotation between the cross members 150, 160 thereby maintaining their orientation with respect to each other.

The elongated insertion arm 168 includes a pin slot 169a defined therethrough that is configured to receive a pin 142 therein. The pin 142 is inserted through a pin hole 159a defined through the elongated receiving arm 158 of the first cross member 150 and through the pin slot 169a of the elongated insertion arm 168 of the second cross member 160 such that the pin 142 slidably translates longitudinally along the pin slot 169a in response to sliding movement between the first and second cross members 150, 160. The sliding movement of the pin 142 in the pin slot 169a helps with rotational alignment and acts as a limit stop for expansion and contraction thereby setting maximum and minimum length dimensions of the transverse connector 100.

The length of the cross member connecting assembly 140 may vary. The length of the cross member connecting assembly 140 (i.e., minimum and maximum length) can range from about 40 mm to about 75 mm. In embodiments, the length of the cross member connecting assembly 140 ranges from about 45 mm to about 48 mm, in some embodiments, the length ranges from about 47 mm to about 52 mm, in some other embodiments, the length ranges about 50 mm to about 58 mm, and in certain embodiments, the length ranges from about 56 mm to about 70 mm.

The elongated insertion arm 168 also includes a threaded set screw receptacle 169b defined therethrough that is configured to receive a cross connector set screw 144 therein. The cross connector set screw 144 includes a threaded body 144a and a recess 145 defined therein that is configured to mate with a driving instrument 10 (FIG. 14). Gripping elements 144b are located within the recess 145 that have a complementary configuration to the driving instrument 10 to control the insertion and/or advancement, as well as retraction and/or withdrawal, of the cross connector set screw 144 into the elongated insertion arm 168.

In operation, when the desired length of the cross member connecting assembly 140 is set, the cross connector set screw 144, which is located within the threaded set screw receptacle 169b of the elongated insertion arm 168, is rotated so as to contact the elongated receiving arm 158 and exert a force thereon to securely lock (i.e., frictional engagement) the elongated insertion arm 168 in its respective position within the elongated receiving arm 158. As the cross connector set screw 144 is tightened, a bottom surface of the cross connector set screw 144 contacts a floor of the receiving passage 159 which causes a top surface of the elongated insertion arm 168 to contact a ceiling of the receiving passage 159 further contributing the frictional engagement between the elongated receiving arm 158 and the elongated insertion arm 168. Rotation of the cross connector set screw 144 in an opposite direction releases the force between the elongated insertion arm 168 and the elongated receiving arm 158 to release the elongated insertion arm 168 from the locked position and again allow sliding motion to reset the length of the cross member connecting assembly 140, as needed or desired.

As shown in FIG. 7, the transverse connector 100 is configured for use in a spinal fixation system or construct 1 which also include pedicle screws or bone screws 2, spinal rods 4, and a band 6. In a method of using the spinal fixation system 1, the pedicle screws 2 are implanted into vertebrae "V" of a spine "S," as required for the surgical procedure, and the spinal rods 4 are positioned within the pedicle screws 2 on opposed sides of the spinous process "SP." The band 6, which is a flexible elongate member, is passed around the lamina "L" of the spine "S" (e.g., with a leader hook (not shown)) with end portions 6a of the band 6 accessible for attachment to the transverse connector 100.

The transverse connector 100 is then placed between the spinal rods 4. The transverse connector 100 may be placed therebetween by holding the transverse connector 100 with a grasping instrument (not shown), as discussed above. With the spinal rod locking screws 130 loosened, the first connection member 110 is snapped onto one spinal rod 4 and the corresponding spinal rod locking screw 130 is provisionally tightened (e.g., with the driving instrument 10 of FIG. 14), and the second connection member 120 is snapped onto the other of the spinal rods 4 and the corresponding spinal rod locking screw 130 is provisionally tightened.

The alignment of the connection members 110, 120 with respect to the cross member connecting assembly 140 may be adjusted by manipulating the respective articulating balls 142, 152 within the corresponding ball joint receptacles 113, 123 and/or adjusting the length of the cross member connecting assembly 140 by sliding the elongated insertion arm 168 to a desired position within the elongated receiving arm 158, as discussed above.

Figure 15A:
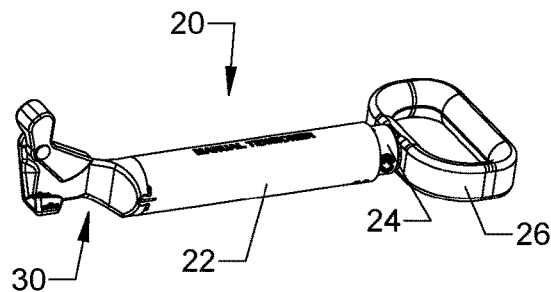
FIG. 15A is a perspective view of a tensioning instrument suitable for use with a band of the spinal fixation systems of FIGS. 7 and 8 in accordance with an embodiment of the present disclosure.

With the band set screws 170 loosened, the band 6 is then attached to the transverse connector 100 by feeding the end portions 6a of the band 6 through the band slots 155, 165 of the transverse connector 100. The band 6 is then tensioned and the band set screws 170 are provisionally tightened (e.g., with the driving instrument 10 of FIG. 14). The band 6 may be tensioned with a manual tensioning instrument 20 (FIG. 15A). To tension the band 6 with the tensioning instrument 20, the tensioning instrument 20 is clamped to the end portion 6a of the band 6 and a handle 26 of the tensioning instrument 20 is pulled until a desired amount of tension is achieved.

Once both end portions 6a of the band 6 are secured to the transverse connector 100 and tensioned to a desired amount, final tightening of the band set screws 170, the spinal rod locking screws 130, and the cross member set screw 144 is effectuated with, for example, the driving instrument 10 (FIG. 14) to complete the construct 1. Excess material at the end portions 6a of the band 6 can then be cut a desired distance from the transverse connector 100 (e.g., 1 cm from the transverse connector 100) and the free extremities thereof may be burned using electrocautery to reduce potential fray. It should be understood that multiple transverse connectors 100 and/or bands 6 may be provided along the length of the spinal rods 4, as needed.

To remove the construct 1, the band set screws 170 are loosen so that the band 6 may be grabbed (e.g., with a forceps (not shown)) to disengage the band 6 from the transverse connector 100. The transverse connector 100 is removed by loosening the spinal rod locking screws 130 and using, for example, a grasping instrument (not shown) to disengage the connection members 110, 120 from the respective spinal rods 4.

Figure 8:
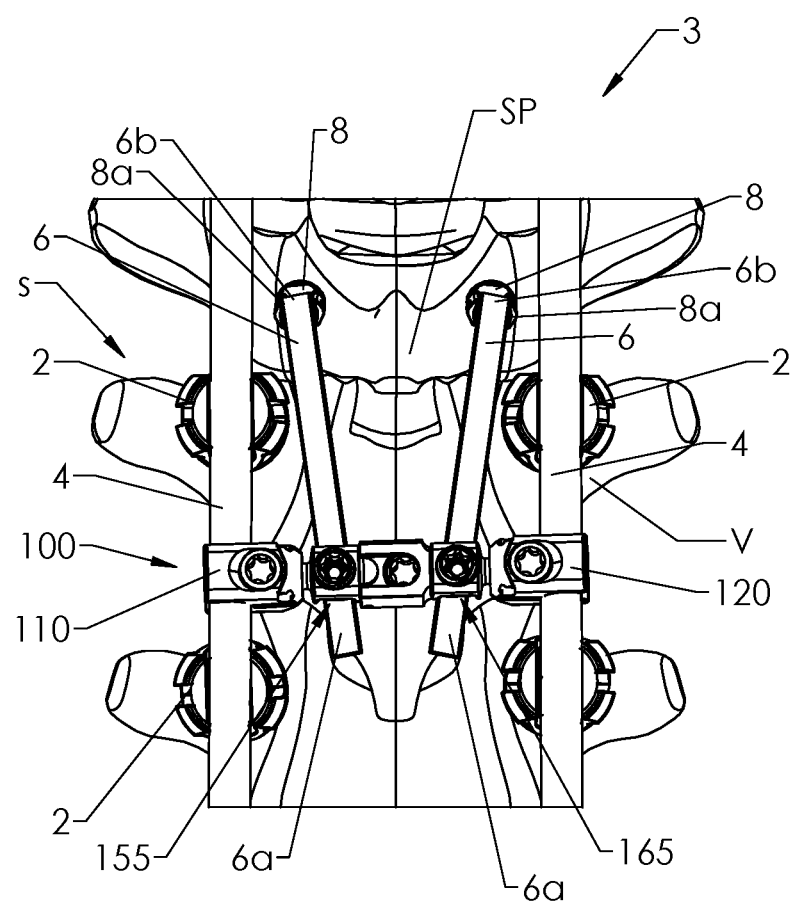
FIG. 8 is a perspective view of a spinal fixation system attached to a spine in accordance with another embodiment of the present disclosure.
Figure 9:
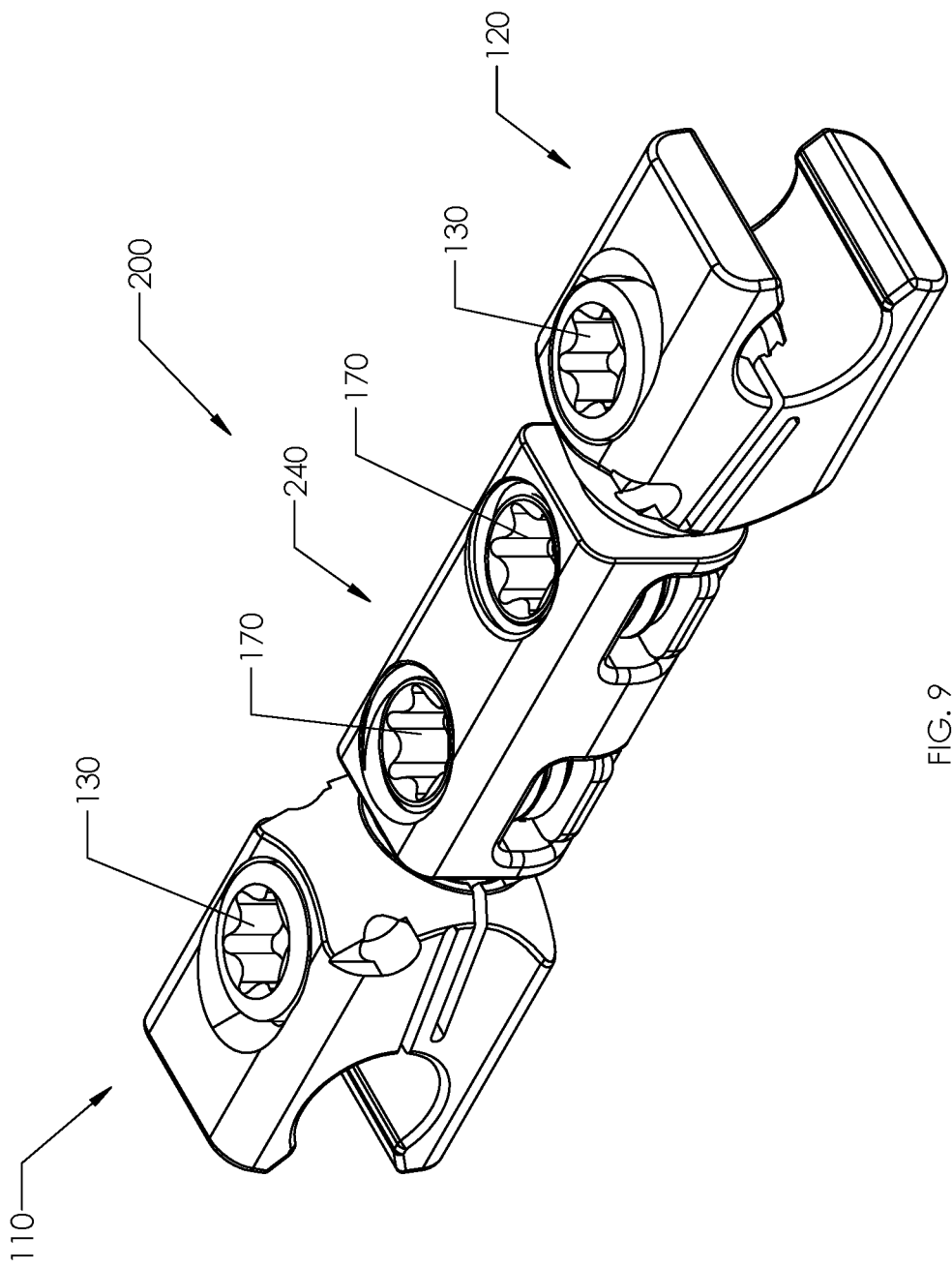
FIG. 9 is a perspective view of a transverse connector in accordance with another embodiment of the present disclosure.
Figure 10:
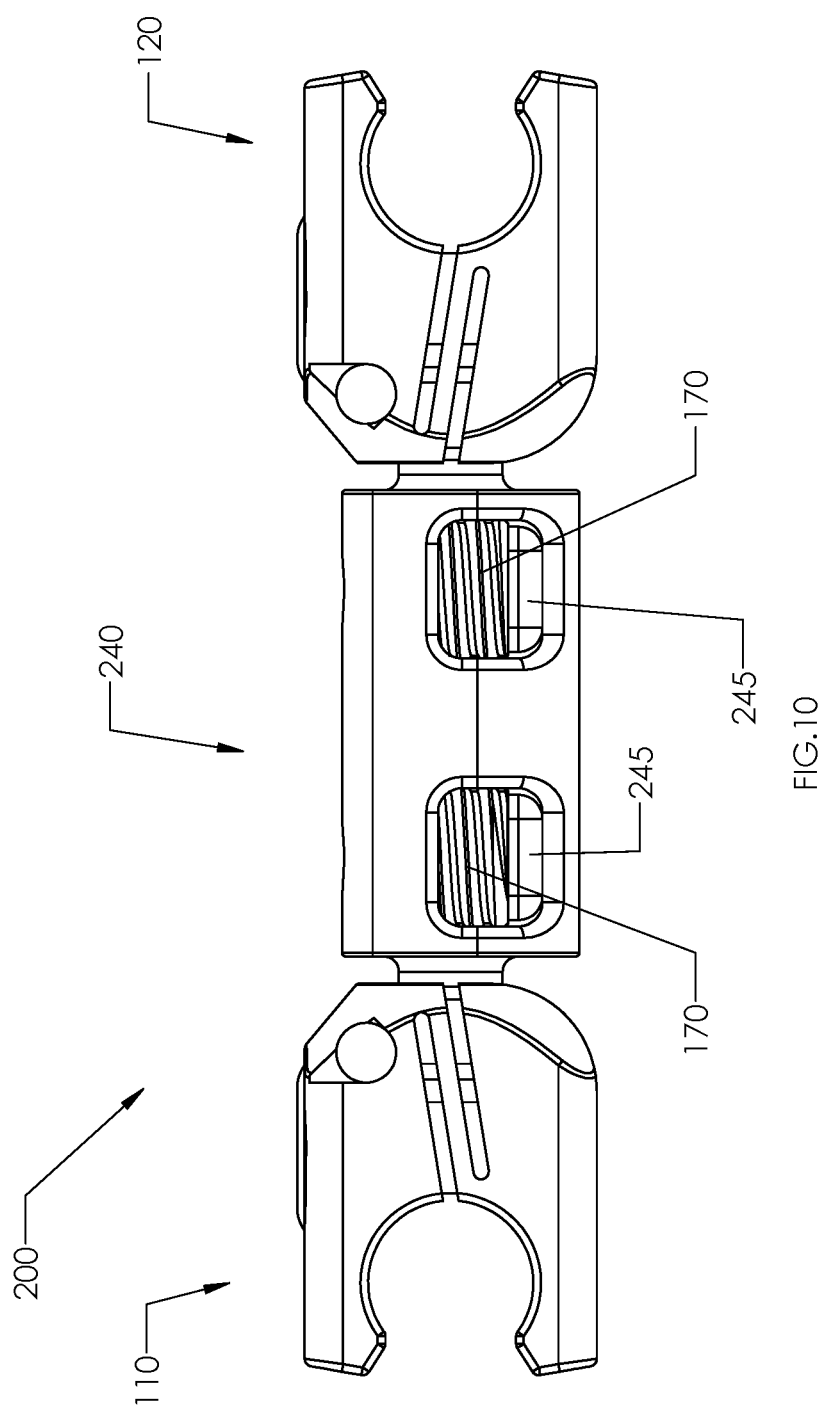
FIG. 10 is a side view of the transverse connector of FIG. 9.
Figure 11:
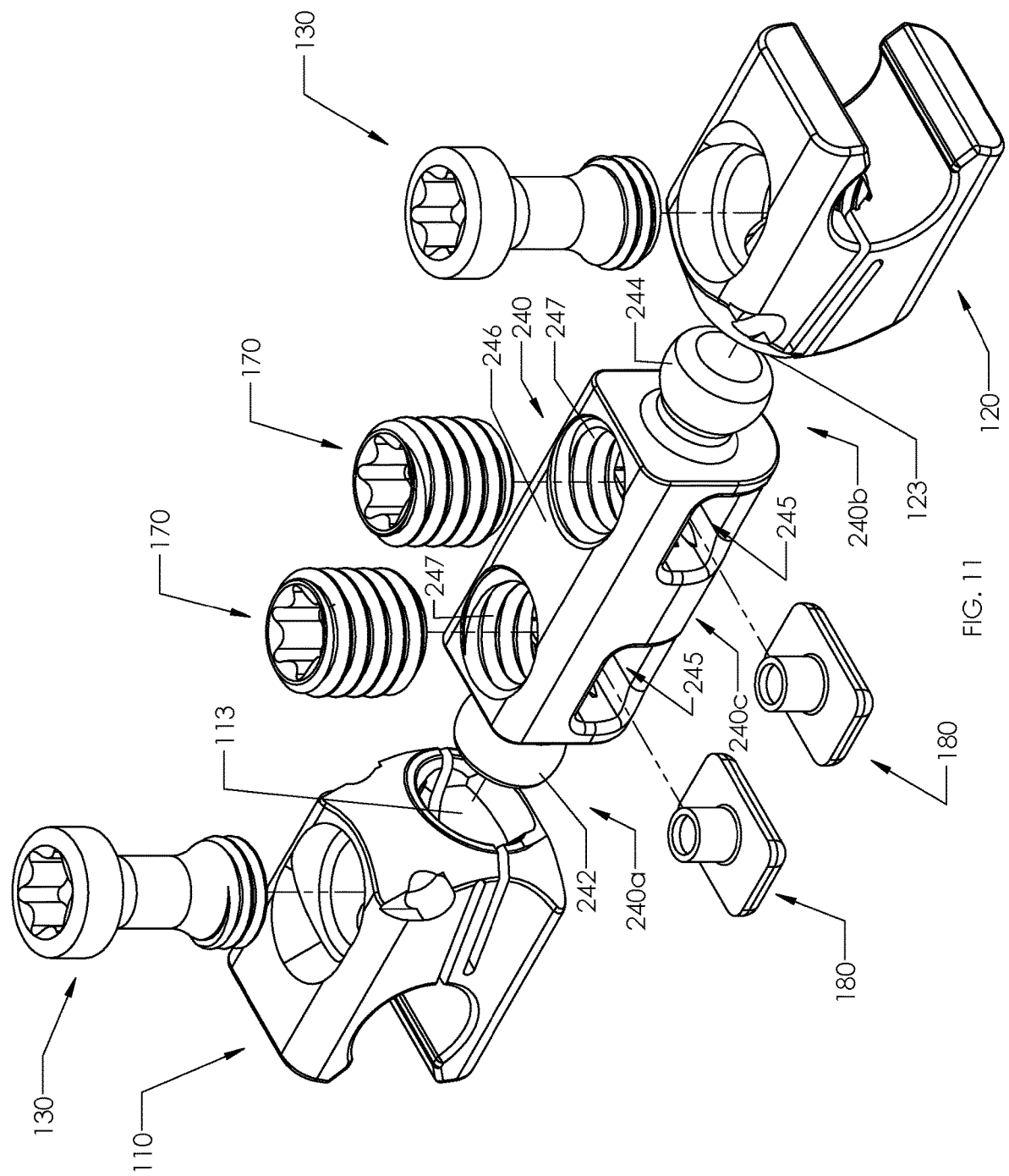
FIG. 11 is a perspective view, with parts separated, of the transverse connector of FIG. 9.
Figure 12:
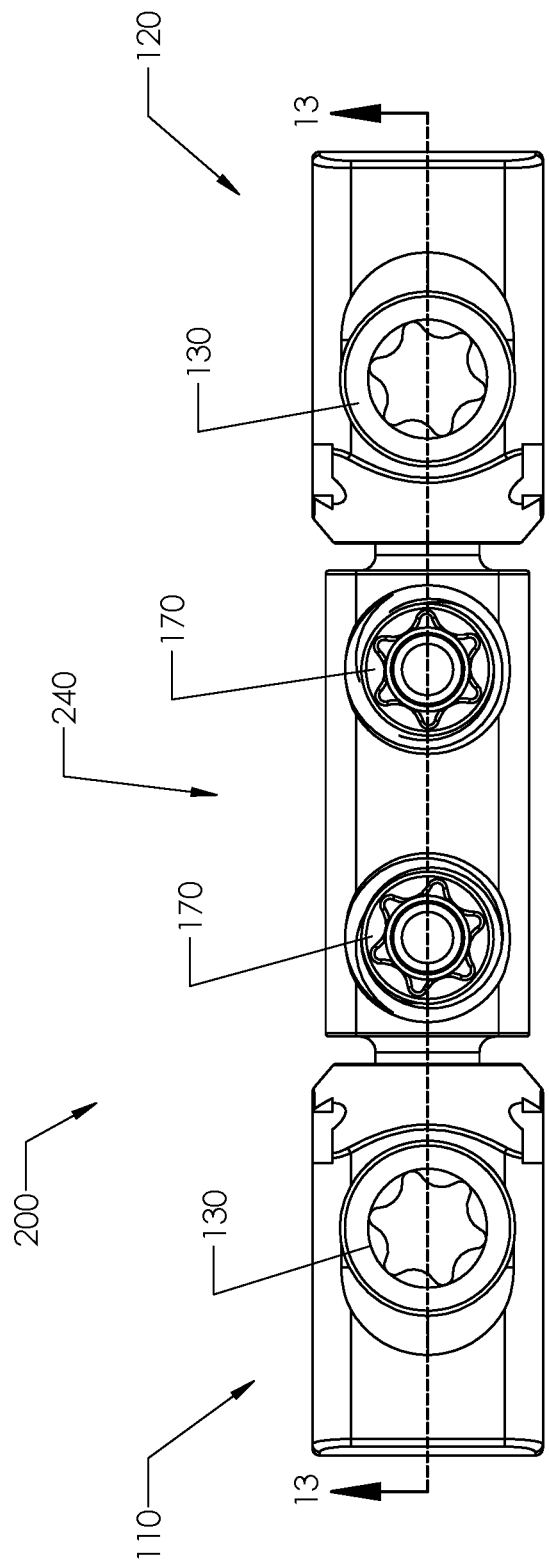
FIG. 12 is a top view of the transverse connector of FIG. 9.
Figure 13:
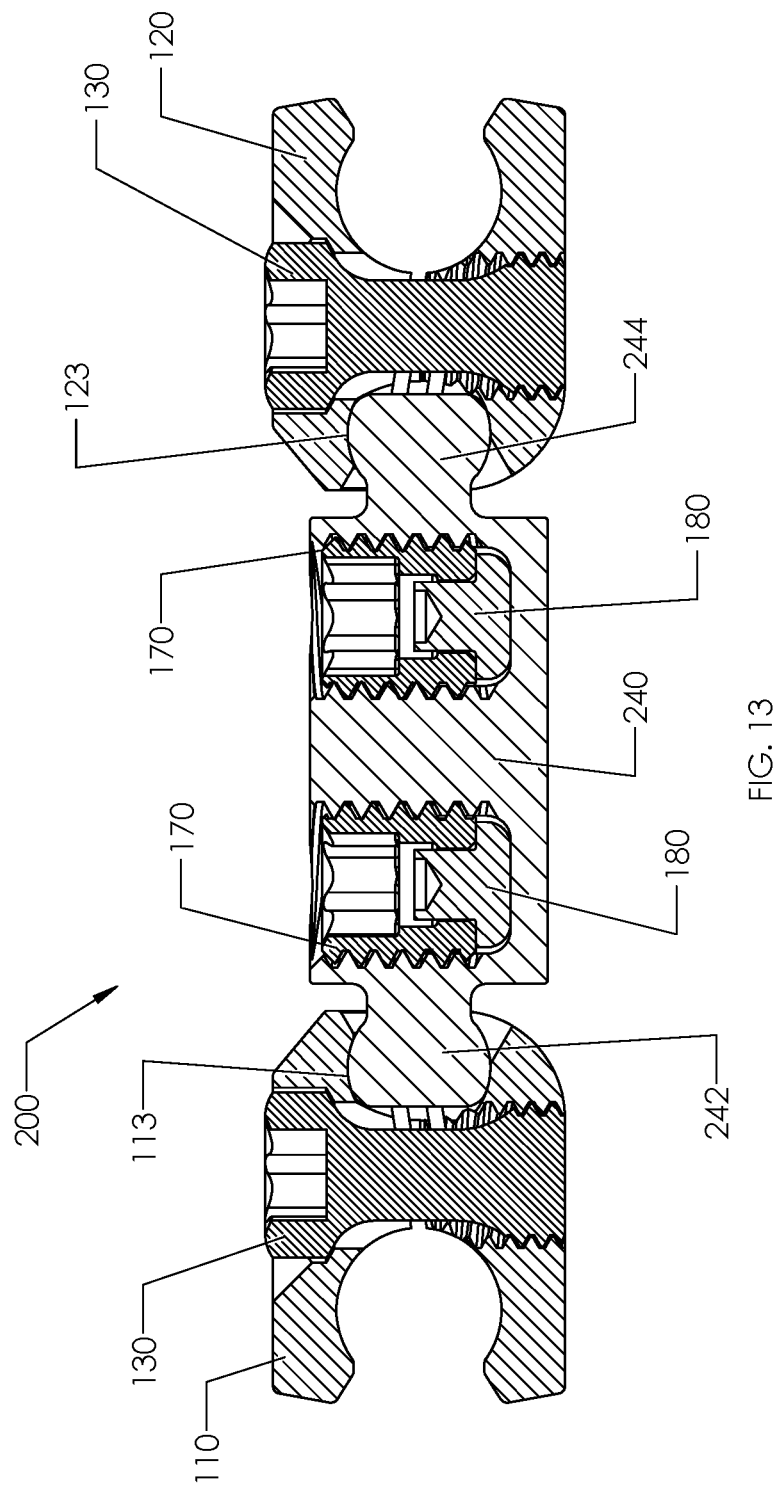
FIG. 13 is a cross-sectional view of the transverse connector of FIG. 9, taken along section line 13-13 of FIG. 12.

As shown in FIG. 8, the transverse connector 100 is configured for use in a spinal fixation system or construct 3 which also includes pedicle screws or bone screws 2, spinal rods 4, bands 6, and bone anchors 8. In a method of using the spinal fixation system 3, the pedicle screws 2 are implanted into vertebrae "V" of a spine "S," as required for the surgical procedure, and the spinal rods 4 are positioned within the pedicle screws 2 on opposed sides of the spinous process "SP."

Bands 6 are also positioned on opposed sides of the spinous process "SP". Each band 6 is threaded through the eyelet 8a of a bone anchor 8 such that a central portion 6b of the band is looped around the eyelet 8a of the bone anchor 8 and the bone anchors 8 are screwed into a bony element of spine "S". The bone anchor 8 may be secured to an anchor insertion instrument (not shown) by attaching an end of the anchor insertion instrument to a head of the bone anchor 8 and feeding the free end portions 6a of the band 6 through a cannula of the anchor insertion instrument. The bone anchor 8 is then screwed into the bony element and the anchor insertion instrument is removed.

The transverse connector 100 is then placed between the spinal rods 4 and secured thereto, as discussed above. The bands 6 are attached to the transverse connector 100 by feeding the two free end portions 6a of each of the bands 6 through the respective band slots 155, 165 of the transverse connector 100 and tensioning the bands 6, as discussed above. Final tightening of the construct 3 and removal of excess band material, if desired, may then be performed, as discussed above.

The construct 3 may be removed by removing the bands 6 from the transverse connector 100 and disengaging the transverse connector 100 from the spinal rods 4, as discussed above. The bone anchors 8 may also be removed by, for example, reengaging the anchor insertion instrument with the bone anchor 8 and rotating the bone anchor 8 in an opposite direction to disengage the bone anchor 8 from the bone.

With reference now to FIGS. 9-13, a transverse connector 200 in accordance with another embodiment of the present disclosure is shown. The transverse connector 200 is substantially similar to the transverse connector 100 of FIGS. 1-6 and will be described with respect to the differences therebetween. The transverse connector 200 includes first and second spinal rod connection members or polyaxial heads 110, 120 and a cross member connecting assembly or bridge assembly 240 connecting the first and second spinal rod connection members 110, 120. The cross member 240 has a fixed or set length.

The cross member connecting assembly 240 includes opposing end portions 240a, 240b including first and second articulating balls 242, 244 that are sized and configured to fit into and articulate within the respective ball joint receptacle 113, 123 of the connection members 110, 120. A middle or central portion 240c of the cross member connecting assembly 240 includes a body 246 defining band slots 245 therethrough and threaded openings 247 configured to threadingly engage a band set screw 170 to secure a band in the respective band slot 245 via engagement with a band anvil 180.

The cross member connecting assembly 240 may be of any length and may include a single band slot 245 therethrough, or multiple band slots 245, and associated band set screws 170 and band anvils 180. The length of the cross member connecting assembly 240 can range from about 30 mm to about 50 mm. In embodiments, the length of the cross member connecting assembly 240 is about 34 mm, in some embodiments, the length is about 37 mm, in some other embodiments, the length is about 40 mm, and in certain embodiments, the length is about 43 mm.

The transverse member 200 is used in a similar manner as discussed above with regard to the transverse connector 100. In embodiments, a caliper (not shown) may be utilized to measure the appropriate length between the spinal rods so that a clinician can choose the best fitting transverse connector 100, 200 option. In embodiments in which a transverse connector having a single band slot is utilized, both ends of a single band or the ends of two bands may be threaded through the single band slot and the ends of the band(s) positioned therethrough may be tensioned simultaneously.

Any of the articulating surfaces of the transverse connectors can be treated, machined, scored, or in any known manner textured to provide a roughened surface that can serve to increase the locking contact of those surfaces when the articulating members are set in place and the associated locking/set screws are manipulated to lock the device in the desired configuration.

The transverse connectors of the present disclosure can be manufactured as components by methods known in the art, to include, for example, molding, casting, forming or extruding, and machining processes. The components can be manufactured using materials having sufficient strength, resiliency, and biocompatibility, as is known in the art for such devices. By way of example only, suitable materials can include implant grade metallic materials, such as titanium, cobalt chromium alloys, stainless steel, or other suitable materials for this purpose. It is also conceivable that some components of the device can be made from plastics, composite materials, and the like.

Referring now to FIG. 14, a driving instrument or driver suitable for use with either the transverse connectors 100, 200 is provided and generally identified by reference numeral 10. The driving instrument 10 includes an elongate shaft 12 having a proximal portion 12a and an opposed distal portion 12b. The proximal portion 12a of the elongate shaft 12 defines a handle or handle attachment feature 14 that is configured to enable selective rotation of the driving instrument 10 (e.g., by gripping the handle 14 with a driver handle (not shown) and applying rotational force thereto) by a clinician. The distal portion 12b of the driving instrument 10 tapers to a driving, but reduced diameter engagement region or tip 16. The engagement region 16 includes protrusions and recesses that are complementary to the recess 133 of the spinal rod locking screws 130, the recess 175 of the band set screws 170, and/or the recess 145 of the cross connector set screw 144. Once the engagement region 16 is inserted into the recess 133, 175, 145, rotation of the driving instrument 10 results in rotation of the respective locking/set screw 130, 170, 144 for inserting and/or removing the locking/set screw 130, 170, 144 into and/or from the respective component of the transverse connector 100, 200.

Figure 15B:
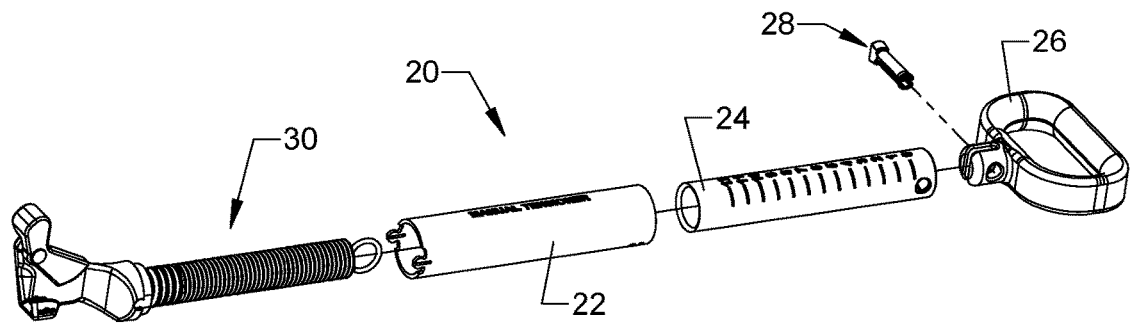
FIG. 15B is a perspective view, with parts separated, of the tensioning instrument of FIG. 15A.
Figure 15C:
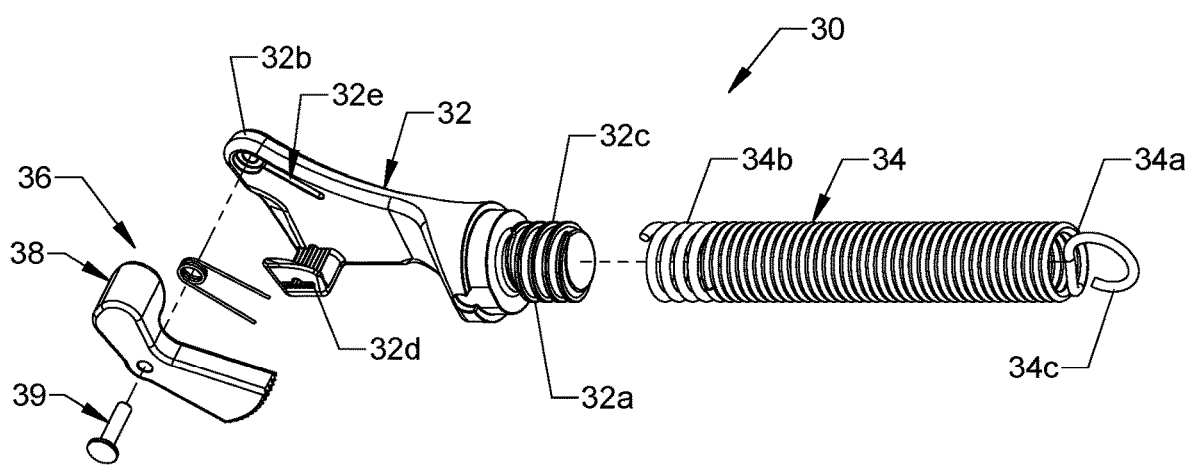
FIG. 15C is a perspective view, with parts separated, of a body assembly of the tensioning instrument of FIG. 15A.

With reference now to FIGS. 15A-15C, a manual tensioning instrument or tensioner suitable for use with the band 6 is provided and generally identified by reference numeral 20. The tensioning instrument 20 includes a body assembly 30, an outer shaft 22, an inner shaft 24, a handle 26, and an assembly pin 28. The outer shaft 22 is coupled to the body assembly 30, and the assembly pin 28 couples the handle 26, the inner shaft 24, and the body assembly 30 together. The body assembly 30 includes a body 32 having a proximal end 32a including a threaded projection 32c and a distal end 32b including a band guide 32d and defining a torsion spring recess 32e. The body assembly 30 includes a tension spring 34 having a proximal end 34a including a loop 34c that couples to the assembly pin 28, and a distal end 34b that secures to the threaded projection 32c of the body 32. The body assembly 30 further includes a torsion spring 36, a cam 38, and a press pin 39 that couples the cam 38 and the torsion spring 36 to the body 32. The torsion spring 36 is seated within the torsion spring recess 32e to spring bias the cam 38 relative to the body 32 as a band 6 (FIG. 7) is drawn between the cam 38 and the band guide 32d.

The transverse connectors, constructs, components thereof, and/or instruments utilized with the transverse connector, constructs, and/or components thereof, may be provided in a kit. The kit is an assembled package that can be provided as a sterile package to facilitate opening and immediate use in an operating room. The kit includes at least one transverse connector. In embodiments, the kit includes a plurality of transverse connectors 140, 240 in a variety of lengths and/or dimensions to allow a clinician to pick and choose one or more suitable transverse connectors (e.g., fixed length or adjustable length) for a surgical procedure. Different transverse connectors 140, 240 may provide additional flexibility for the spinal rod and screw construct by, for example, having different minimum to maximum lengths. The kit may further include additional orthopedic devices (e.g., pedicle screws, hooks, spinal rods, bands, and/or anchors), and/or instruments (e.g., driving instruments, grasping instruments, tensioning instruments, anchor inserting instruments, calipers, forceps, leader hooks, etc.) suitable for use with the transverse connectors and/or additional orthopedic devices.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A transverse connector comprising:
   a cross member connecting assembly including a first band slot defined therethrough, the cross member connecting assembly defining an axis, the first band slot defined entirely through the cross member connecting assembly in a direction transverse to the axis, and a threaded opening extending through an upper surface of the cross member connecting assembly and into the first band slot, the cross member connecting assembly including a band set screw threadingly engaged with the threaded opening and movable relative to the first band slot and a band anvil non-rotatably coupled to the band set screw, the band anvil including a plate disposed within the first band slot such that rotation of the band set screw results in the plate varying spacing within the first band slot; and
   first and second spinal rod connection members rotatably engaged with opposing end portions of the cross member connecting assembly.

2. The transverse connector according to claim 1, wherein the band set screw includes a channel defined therein and including an annular rim, and the band anvil includes a stem extending from the plate and including an annular flange, the stem positioned within the channel with the annular flange engaged with the annular rim.

3. The transverse connector according to claim 1, wherein the cross member connecting assembly has a fixed length.

4. The transverse connector according to claim 3, wherein the cross member connecting assembly further includes a second band slot defined therethrough and a second threaded opening extending through an upper surface of the cross member connecting assembly and into the second band slot, the cross member connecting assembly including a second band set screw threadingly engaged with the second threaded opening and movable relative to the second band slot.

5. The transverse connector according to claim 1, wherein the cross member connecting assembly includes a first cross member and a second cross member slidably engaged with each other, and the first band slot is defined in the first cross member.

6. The transverse connector according to claim 5, wherein the second cross member includes a second band slot defined therethrough and a second threaded opening extending through an upper surface of the cross member connecting assembly and into the second band slot, the cross member connecting assembly including a second band set screw threadingly engaged with the second threaded opening and movable relative to the second band slot.

7. The transverse connector according to claim 5, wherein the first cross member includes an elongated receiving arm and the second cross member includes an elongated insertion arm slidably disposed within a receiving passage of the elongated receiving arm.

8. The transverse connector according to claim 7, wherein the elongated receiving arm includes a pin hole defined therethrough and the elongated insertion arm includes a pin slot defined therethrough, and a pin is positioned through the pin hole and the pin slot such that the pin slidably translates longitudinally in the pin slot in response to sliding movement between the first and second cross members.

9. The transverse connector according to claim 7, wherein the elongated insertion arm includes a threaded set screw receptacle defined therein, and a cross connector set screw rotatably coupled with the threaded set screw receptacle.

10. The transverse connector according to claim 1, wherein the opposing end portions of the cross member connecting assembly includes first and second articulating balls, respectively, the first articulating ball disposed within a first ball joint receptacle of the first spinal rod connection member and the second articulating ball disposed within a second ball joint receptacle of the second spinal rod connection member.

11. A spinal fixation construct comprising:
   a plurality of bone screws;
   spinal rods; and
   a transverse connector including:
      a cross member connecting assembly having a fixed length and including first and second band slots defined therethrough, the cross member connecting assembly defining an axis, the first and second band slots defined entirely through the cross member connecting assembly in a direction transverse to the axis, a first threaded opening extending through an upper surface of the cross member connecting assembly and into the first band slot, and a second threaded opening extending through an upper surface of the cross member connecting assembly and into the second band, the cross member connecting assembly including a first band set screw threadingly engaged with the first threaded opening and movable relative to the first band slot and a second band set screw threadingly engaged with the second threaded opening and movable relative to the second band slot; and first and second spinal rod connection members rotatably engaged with opposing end portions of the cross member connecting assembly, the first and second spinal rod connection members including respective first and second spinal rod connection passages defined therethrough for selectively and releasably securing the spinal rods thereto.

12. The spinal fixation construct according to claim 11, further including a band, the band positionable through the band slot of the cross member connecting assembly and securable therein by the band set screw.

13. The spinal fixation construct according to claim 12, further including a bone anchor, the band including a central portion positionable around an eyelet of the bone anchor and end portions positionable through the band slot of the cross member connecting assembly.

14. A method for spinal stabilization, comprising:
attaching a first spinal rod connection member of a transverse connector to a first spinal rod, the transverse connector defining an axis and a band slot, the band slot defined entirely through the transverse connector;
attaching a second spinal rod connection member of the transverse connector to a second spinal rod, the first and second spinal rods disposed on opposed sides of a spinous process of a spine such that a cross member connecting assembly of the transverse connector extends between the first and second spinal rods;
attaching an end portion of a band through the band slot in a direction transverse to the axis;
placing bone anchors into a bony element of the spine; and
passing a band through each of the bone anchors such that a central portion of each of the bands is looped around and eyelet of the respective bone anchor and end portions of the band are passed through band slots defined through the cross member connecting assembly.

15. The method according to claim 14, further comprising tightening spinal rod locking screws into respective first and second spinal rod locking screw receptacles of the first and second spinal rod connection members after attaching the first and second spinal rod connection members to the first and second spinal rods.

16. The method according to claim 14, further comprising tightening a cross connector set screw into a threaded set screw receptacle of an elongated insertion arm of the second cross member that is disposed within a receiving passage of an elongated receiving arm of the first cross member after adjusting the length of the cross member connecting assembly.

17. The method according to claim 14, further comprising:
looping a band around a lamina of the spine; and
passing end portions of the band through a band slot defined through the cross member connecting assembly.

18. The method according to claim 17, further comprising:
tensioning the band; and
tightening a band set screw into a threaded opening of the cross member connecting assembly, the threaded opening extending into the band slot such that the band set screw is movable into the band slot to secure the end portions of the band within the band slot.

* * * * *